United States Patent
Kojiri et al.

(10) Patent No.: US 6,703,373 B1
(45) Date of Patent: Mar. 9, 2004

(54) INDOLOPYRROLOCARBAZOLE DERIVATIVES AND ANTITUMOR AGENTS

(75) Inventors: Katsuhisa Kojiri, Tokyo (JP); Hisao Kondo, Tsukuba (JP); Hiroharu Arakawa, Tsukuba (JP); Mitsuru Ohkubo, Tsukuba (JP); Hiroyuki Suda, Tokyo (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/070,825

(22) PCT Filed: Sep. 10, 1999

(86) PCT No.: PCT/JP99/04911

§ 371 (c)(1),
(2), (4) Date: Mar. 11, 2002

(51) Int. Cl.$^7$ .................. A01N 43/04; A61K 31/70; C07H 15/00; C07H 19/00; C07H 19/22
(52) U.S. Cl. .................. 514/43; 514/27; 536/17.7; 536/18.7; 536/27.1; 536/28.1
(58) Field of Search .................. 514/27, 43; 536/17.7, 536/18.7, 27.1, 28.1

(56) References Cited

U.S. PATENT DOCUMENTS

| | | | |
|---|---|---|---|
| 5,591,842 A | * | 1/1997 | Kojiri et al. |
| 5,668,271 A | | 9/1997 | Kojiri et al. |
| 5,804,564 A | | 9/1998 | Kojiri et al. |

FOREIGN PATENT DOCUMENTS

| | | | |
|---|---|---|---|
| EP | 0 388 956 A2 | | 9/1990 |
| EP | 0 528 030 A1 | | 2/1993 |
| EP | 0 545 195 A1 | | 6/1993 |
| JP | A2-10-245390 | * | 9/1998 |
| WO | WO 96/04293 | | 2/1996 |

* cited by examiner

Primary Examiner—James O. Wilson
Assistant Examiner—Traviss C. McIntosh, III
(74) Attorney, Agent, or Firm—Nixon & Vanderhye P.C.

(57) ABSTRACT

A compound represented by the formula or a pharmaceutically acceptable salt thereof

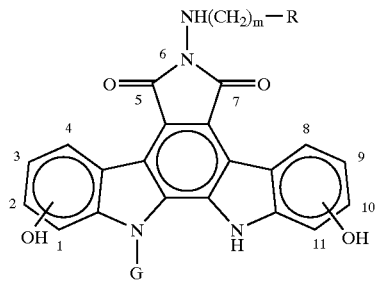

[I]

wherein R represents an unsubstituted pyridyl, furyl or thienyl group, or a pyridyl, furyl or thienyl group each of which has one or more substituents selected from the group consisting of a hydroxyl group, a lower alkoxy group, a hydroxy lower alkyl group and a hydroxy lower alkenyl group except that when the pyridyl, furyl or thienyl group has a lower alkoxy group as a substituent, each of which simultaneously has another substituent selected from the group consisting of a hydroxyl group, a lower alkoxy group, a hydroxy lower alkyl group and a hydroxy lower alkenyl group, m represents an integer of 1 to 3, and G represents a β-D-glucopyranosyl group, and the positions of substitution of the hydroxyl groups on the indolopyrrolocarbazole ring are the 1- and 11-positions, or the 2- and 10-positions, and an antitumore agent containing it as an effective ingredient.

The compounds have a better antitumor action than known compounds having a similar structure.

12 Claims, No Drawings

INDOLOPYRROLOCARBAZOLE DERIVATIVES AND ANTITUMOR AGENTS

TECHNICAL FIELD

This invention is useful in the pharmaceutical field, and, more detailedly, relates to novel indolopyrrolocarbazole derivatives inhibiting growth of tumor cells and exerting antitumor effect, and their use as antitumor agents.

BACKGROUND ART

Many compounds are already put to practical use as pharmaceuticals in the field of tumor chemotherapy. However, their effects are not always sufficient against various kinds of tumors, and the problem of resistance of tumor cells to these drugs also makes the methods of clinical use complicate (see, Proceedings of the 47th Annual Meeting of Japan Cancer Society, pages 12–15, 1988).

Under the circumstances, development of novel anticancer substances is always desired in the field of cancer treatment. Particularly, there is need for substances overcoming resistance to existing carcinostatic substances and showing effectiveness against cancers on which existing carcinostatic substances cannot exert sufficient effect.

Under these present circumstances, the present inventors have widely screened metabolites of microorganisms, and as a result, they found a novel compound BE-13793C (12,13-dihydro-1,11-dihydroxy-5H-indolo[2.3-a]pyrrolo[3,4-c]carbazole-5,7(6H)-dione) having antitumor activity (see, EP-A2-0388956).

Thereafter, they have tried to create compounds having further excellent antitumor activity by chemically modifying BE-13793C, and disclosed such compounds in prior patent applications and patents (EP-A1-0528030, U.S. Pat. Nos. 5,591,842, 5,668,271 and 5,804,564, WO95/30682 and WO96/04293).

U.S. Pat. No. 5,668,271 discloses a wide range of compounds having antitumor activity, including compounds wherein $R_1$ (or $R_2$) is 1) a $C_1$–$C_6$ alkyl group substituted by a $C_6$–$C_{12}$ aromatic hydrocarbon group; or 2) a 5- or 6-membered nonaromatic or aromatic heterocyclic group. The compounds of the present invention have a —(CH$_2$)m-R group (wherein R represents a substituted or unsubstituted group selected from pyridyl, furyl or thienyl) bound to the exocyclic nitrogen instead of $R_1$ (or $R_2$). Furthermore, as disclosed in the instance application, the compounds of the invention have much better antitumor effects than the analogous compounds generically and specifically disclosed in U.S. Pat. No. 5,668,271.

Although, in the structural formula shown in Example 35 of the above U.S. Pat. No. 5,668,271, a group corresponding to —(CH$_2$)$_m$—R in the compounds of the present invention is shown as a 2-pyridylmethyl group, this group should be read a 2-pyridylcarbonyl group. This is apparent from that α-picolinohydrazide is used as a reactant.

Compounds disclosed in the above-mentioned other prior applications and patents are further remoter in structure from the compounds of the present invention. Namely, EP-A1-0528030 solely discloses compounds wherein a group correspoding to —NH—(CH$_2$)$_m$—R in the compounds of the present invention is H. U.S. Pat. No. 5,591,842 discloses compounds wherein groups corresponding to —(CH$_2$)$_m$—R and H bound to N in the compounds of the present invention are $R^1$ and $R^2$ and the $R^1$ and $R^2$ include comprehensive groups, but as compounds closest to the compounds of the present invention, only compounds wherein $R^1$ and $R^2$ are $C_1$–$C_6$ alkyl groups substituted with a $C_6$–$C_{12}$ aromatic hydrcarbonic group, or furyl, thienyl or pyridyl groups (one of $R^1$ and $R^2$ can be H) are disclosed. U.S. Pat. No. 5,804,564 and WO95/30682 solely disclose compounds wherein a group corresponding to —(CH$_2$)$_m$—R in the compounds of the present invention is a bis(hydroxymethyl)methyl group. WO96/04293 discloses compounds wherein a group corresponding to —NH(CH$_2$)$_m$—R in the compounds of the present invention is $R^1$ and this $R^1$ includes comprehensive groups, but compounds close to the compounds of the present invention are not found and, further, a group corresponding to G in the compounds of the present invention is a disaccharide group.

Some of the compounds of the present invention, namely compounds wherein R is a pyridyl, furyl or thienyl group each having a substituent are disclosed in JP-A-10-245390 (published on Sep. 14, 1998), the inventors of which are the applicants of the present application. The JP-A application has not yet been examined and applications to other countries corresponding thereto have not been made except the present application.

From the above, in relation with the above-mentioned background art, the invention of the present application are believed not to be considered at least as an object of rejection under 35 U.S.C. §102 (B) and (D).

DISCLOSURE OF INVENTION

It is a problem to be solved in the present invention to create compounds having further excellent antitumor activity by chemically modifying indolopyrrolocarbazole antitumor substances disclosed in the prior patent applications.

For solving the above problem, the present inventors have synthesized a wide range of indolopyrrolocarbazole derivatives and examined their antitumor or activity, and found that compounds represented by the later-described formula [I] show further excellent antitumor activity than the indolopyrrolocarbazole compounds disclosed in the prior applications, and completed the present invention.

Namely, the invention relates to a compound represented by the formula or a pharmaceutically acceptable salt thereof

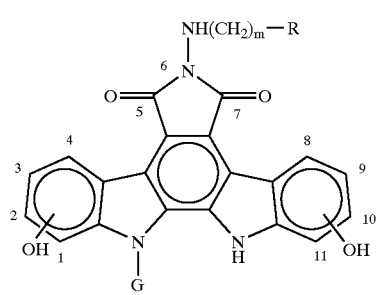

wherein R represents an unsubstituted pyridyl, furyl or thienyl group, or a pyridyl, furyl or thienyl group each of which has one or more substituents selected from the group consisting of a hydroxyl group, a lower alkoxy group, a hydroxy lower alkyl group and a hydroxy lower alkenyl group except that when the pyridyl, furyl or thienyl group has a lower alkoxy group as a substituent, each of which simultaneously has another substituent selected from the group consisting of a hydroxyl group, a lower alkoxy group, a hydroxy lower alkyl group and a hydroxy lower alkenyl group, m represents an integer of 1 to 3, and G represents a β-D-glucopyranosyl group, and the positions of substitution of the hydroxyl groups on the indolopyrrolocarbazole ring are the 1- and 11-positions, or the 2- and 10-positions, and a use thereof as an antitumor agent.

BEST MODE FOR CARRYING OUT THE INVENTION

In the definition of the substituents in the compounds of the invention represented by the formula [I], lower alkoxy groups represent straight-chain or branched alkoxy groups having 1 to 6, preferably 1 to 4, further preferably 1 or 2, most preferably 1 carbon atoms, and there can for example be mentioned a methoxy group, an ethoxy group, a propoxy group, n-butoxy group, s-butoxy group, n-hexyl group, etc.

Hydroxy lower alkyl groups represent straight-chain or branched hydroxyalkyl groups having 1 to 6, preferably 1 to 4, further preferably 1 or 2, most preferably 1 carbon atoms, and there can for example be mentioned a hydroxymethyl group, a hydroxyethyl group, a hydroxypropyl group, a hydroxybutyl group, a hydroxyhexyl group, etc.

Hydroxy lower alkenyl groups represent straight-chain or branched hydroxyalkenyl groups having 2 to 6, preferably 3 or 4, further preferably 3 carbon atoms, and there can for example be mentioned a 3-hydroxy-1-propenyl group, etc. m represents an integer of 1 to 3, preferably 1.

The positions of substitution of the hydroxyl groups on the indolopyrrolocarbazole ring may be the 1- and 11-positions, or the 2- and 10-positions, but the 2- and 10-positions are preferred.

Description is made below on processes for preparing the compounds of the invention.

An indolopyrrolocarbazole derivative of the invention can be prepared by reacting a compound represented by the formula

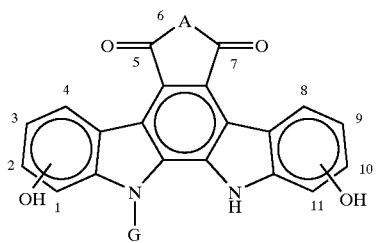 [II]

wherein, A represents NH or H, and G is as defined above, the compound being a known compound disclosed in EP-A1-0528030, EP-A1-0545195, WO95/30682 and WO96/04293, with a compound represented by the formula

 [III]

wherein, R and m are as defined above, or by condensing a compound represented by the formula

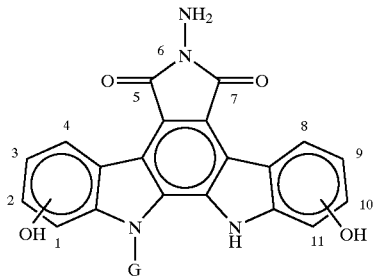 [IV]

wherein, G is as defined above, with a compound represented by the formula

R$^1$(CH$_2$)$_m$CHO [V]

wherein, R$^1$ has the same meaning as R or means R wherein hydroxyl groups are protected, and m is as defined above, then carrying out reduction, and, if necessary, removing the protective groups, or by reacting a compound of the formula [IV] with a compound represented by the formula R$^1$(CH$_2$)$_m$L [VI]

wherein, L means a leaving group, and R$^1$ and m are as defined above, and, if necessary, removing the protective groups.

The reaction between the compound represented by the formula [II] and the compound represented by the formula [III] is reaction between an imide or an acid anhydride and a hydrazine derivative, well-known in the chemical field. This reaction can be carried out using a solvent usually having no bad influenece on the reaction, such as, for example, tetrahydrofuran or N,N-dimethylformamide. The use amount of the compound [III] is usually a little excess to 5 molar equivalents based on the compound [II], but a largely excess use of the former is possible.

The reaction temperature is usually in the range of −50° C. to the boiling point of the solvent, but, if necessary, temperature higher than or lower than the temperature can be used. The reaction time is usually in the range of 30 minutes to 2 days, but time longer than or shorter than the time can be used.

The reaction of preparing a compound [I] by condensing a compound represented by the formula [IV] with a compound represented by the formula [V] and then carrying out reduction can be carried out in the same reaction system, but in some occasion, it is also possible to, once isolate the Schiff base as an intermediate product. Namely usually, the reaction can be carried out by mixing the compound [IV] with the compound [V] in a suitable solvent and then adding a reducing agent. The reaction is preferably carried out in the presence of an acid such as acetic acid or hydrochloric acid. As usable solvents, there can, for example, be mentioned alcoholic solvents such as methanol and ethanol, aprotic polar solvents such as N,N-dimethylformamide, etc. The reduction of the Schiff base can be carried out using a metal hydride complex such as sodium cyanoborohydride, or the like, and also by catalytic reduction.

The reaction between a compound [IV] and a compound [VI] is alkylation reaction of an amine, and can be carried out by a known method, for example by reaction with an alkyl halide, alkyl mesylate or alkyl tosylate or the like.

The products of the above reactions can be purified by methods known in the field of organic chemistry, for example by precipitation methods, solvent extraction methods, recrystallization, chromatography, etc.

Further in the invention, pharmaceutically acceptable salts of compounds obtained by the above processes are included. As such salts, there can be mentioned salts with an alkali metal such as for example potassium or sodium, salts with an alkaline earth metal such as for example calcium, salts with a basic organic compound such as for example ethylamine or arginine, salts with an inorganic acid such as hydrochloric acid or sulfuiric acid, and salts with an organic acid such as acetic acid, citric acid or maleic acid.

The compounds of the invention represented by the formula [I] show excellent antitumor action.

Growth Inhibition Activity on Mouse Leukemia Cells

100 μl of a medium for cell culture (RPMI-1640 medium containing 10% fetal bovine serum) containing $3 \times 10^3$ mouse leukemia cells (P388) was put in a 96-well microplate, and culture was carried out at 37° C. for 24 hours under 5% $CO_2$. 10 μl of a medium containing a test compound was added, and culture was continued at 37° C. for further 24 hours under 5% $CO_2$. 10 μl of 0.5% Thiazoyl Blue was added to the cultured medium, and incubation was made at 37° C. for 2 hours under 5% $CO_2$ to carry out enzymatic reaction. 20% sodium dodecyl sulfate (SDS) was added to discontinue the reaction, and incubation was carried out at 37° C. for further 4 hours to dissolve the resulting dye, and absorbance at 550 nm was measured and compared with the control group. The results are shown in Table 1.

Growth Inhibition Activity on Human Gastric Cancer Cells, Human Colon Cancer Cells and Human Lung Cancer Cells 100 μl of a medium for cell culture (RPMI-1640 medium containing 10% fetal bovine serum) containing $1 \times 10^4$ human gastric cancer cells (MKN-45), human colon cancer cells (DLD-1) or human lung cancer cells (PC-13) was put in a 96-well microplate, and culture was carried out at 37° C. for 24 hours under 5% $CO_2$. 100 μl of a medium containing a test compound was added, and culture was continued at 37° C. for further 72 hours under 5% $CO_2$. After completion of the culture, 50 μl of 50% trichloroacetic acid was added to the cultured medium, and the mixtures were held at 4° C. for 60 minutes to fix the cells. The cultured medium containing trichloroacetic acid was removed, and the wells were washed with tap water and dried. 50 μl of 0.4% Sulforhodamine B solution was added, and the mixtures were held at room temperature for 30 minutes to dye the cells. The dyeing solutions were removed, and the remaining dyeing solutions were washed away with 1% acetic acid. After complete removal of the acetic acid solution and drying, 200 μl of 10 nM Tris solution was added and the mixtures were mixed well at room temperature for 1 hour or more to extract the dye. Absorbance of each well at 560 nm was measured, and the inhibition proportion in comparison with the group of no addition of any drug was calculated. The results are shown in Table 1.

TABLE 1

Growth inhibition activity on some tumor cells

| Test compound | 50% inhibition concentration ($IC_{50}$, nM) | | | |
|---|---|---|---|---|
| | P-388 | MKN-45 | DLD-1 | PC-13 |
| Example 3 | 0.28 | 0.35 | 0.91 | 0.22 |
| 15 | 0.50 | 2.10 | 4.3 | 0.62 |
| 16 | 0.40 | 1.30 | 4.0 | 0.56 |
| 18 | 0.43 | 0.66 | 4.6 | 0.30 |
| 19 | 0.19 | 0.92 | 1.3 | 0.50 |
| 20 | 0.87 | 0.92 | 1.0 | 0.67 |
| 22 | 0.63 | 1.80 | 1.0 | 0.58 |
| 23 | 0.48 | 1.50 | 8.9 | 2.3 |

TABLE 1-continued

Growth inhibition activity on some tumor cells

| Test compound | 50% inhibition concentration ($IC_{50}$, nM) | | | |
|---|---|---|---|---|
| | P-388 | MKN-45 | DLD-1 | PC-13 |
| 24 | 0.48 | 0.71 | 3.3 | 0.27 |
| Control compound 1 | 190 | 39 | 8200 | 710 |
| Control compound 2 | 6.5 | 12.0 | 76 | 48.0 |

Control compound 1: a compound of the formula [I] of the present invention wherein —AAAAAAA($CH_2$)$_m$—R is a 2-pyridyl group and the positions of substitution of the hydroxyl groups on the indolopyrrolocarbazole ring are the 1- and 11-positions. The control compound 1 is disclosed in Example 15 of U.S. Pat. No. 5,668,271.

Control compound 2: a compound of the formula [I] of the present invention wherein —($CH_2$)$_m$—R is a 3-hydroxybenzyl group and the positions of substitution of the hydroxyl groups on the indolopyrrolocarbazole ring are the 1- and 11-positions. The control compound 1 is disclosed in Example 23 of U.S. Pat. No. 5,668,271.

Antitumor Effect on Human Gastric Cancer (MKN-45), Human Breast Cancer (MX-1) and Human Colon Cancer (LS180)

A MKN-45, MX-1 or LS180 solid tumor previously subcutaneously implanted in a nude mouse and grown was thinly cut, and its cubes with each side 3 mm were subcutaneously implanted in test mice. After the implantation, starting from the time when the tumor grew into 0.3 cm³ or more, various dosages of a test compound were injected once a day for 5 consecutive days into the tail veins of the mice. The same injections were then made for further 5 days after 2 days of interval (treatment schedule: 5/w×2) or once every 3–4 days, four times in total (treatment schedule: 2/w×2). 28 after the start of the treatment, the length (L) and the breadth (W) of each of the tumors were measured, and its volume (V) was calculated (V=½×L×W²). A tumor growth inhibition proportion was calculated based on the volume, and a total dose to inhibit tumor growth by 75% ($GID_{75}$, mg/m² body surface area) was then determined. The results are shown in Table 2.

TABLE 2

Antitumor action on mice carrying various tumors

| | $GID_{75}$(mg/m² total) | | |
|---|---|---|---|
| Test compound | Human gastric cancer MKN-45 | Human breast cancer MX-1 | Human colic cancer LS180 |
| Example 3 | <30 | <12 | 48 |
| 15 | <90 | <6 | 400 |
| 16 | | <36 | |
| 18 | | 16 | |
| 19 | | <30 | |
| 20 | | <30 | |
| 23 | | 19 | |
| 24 | 12 | 27 | 114 |
| Control compound | 370 | 97 | 1900 |

Control compound: a compound of the formula [I] of the present invention wherein —($CH_2$)$_m$—R is a 3-hydroxybenzyl group and the positions of substitution of the hydroxyl groups on the indolopyrrolocarbazole ring are the 2- and 10-positions. This control compound is not specifically disclosed in U.S. Pat. No. 5,668,271, but is an isomer of the compound disclosed in Example 23 of the U.S. Patent, both compounds differing in the positions of substitution of the hydroxyl groups on the indolopyrrolocrbazole ring.

Compounds provided by the present invention show a much better antitumor action than the control compounds, as shown in the above pharmacological test results.

As apparent from the results of the above pharmacological tests, the compounds of the invention show an excellent antitumor action, and are useful as antitumor agents for humans or other mammals, particularly humans, for prophylaxis and/or treatment of, for example, head or neck cancer, thyroid cancer, lung cancer, esophageal cancer, gastric cancer, hepatic cancer, pancreatic cancer, colon cancer, renal cancer, prostate cancer, testoid cancer, uterine cancer, ovarian cancer, breast cancer, brain cancer, etc. as solid cancers, and leukemia, lymphoma, myeloma, etc. as other cancers, preferably gastric cancer, colon cancer, lung cancer and breast cancer.

A compound of the invention can be used in the form of antitumor pharmaceutical preparations suitable for oral administration, parenteral administration, etc., obtained by mixing the compound with solid or liquid excipients or carriers known in the field of pharmaceutical preparations. As forms for oral administration, there can be mentioned peroral agents such as for example tablets, capsuls, powders, granules and liquids, and as forms for parenteral administration, there can be mentioned sterilized liquid parenteral agents such as for example solutions and suspensions.

Solid preparations such as tablets, capsules, granules and powders can be prepared using compounds of the invention alone, but can also be prepared further using suitable additives. As the suitable additives, there can be mentioned conventional additives, for example, sugars such as for example lactose and glucose, starches such as for example corn, wheat and rice, fatty acids such as for example stearic acid, inorganic salts such as for example magnesium metasilicate aluminate and anhydrous calcium phosphate, synthetic macromolecules such as for example polyvinylpyrrolidone and polyalkylene glycols, fatty acid salts such as for example calcium stearate and magnesium stearate, alcohols such as for example stearyl alcohol and benzyl alcohol, synthetic cellulose derivatives such as for example methylcellulose, carboxymethylcellulose, ethylcellulose and hydroxypropylmethylcellulose, and further, water, gelatin, talc, vegetable oils, gum arabic, etc.

These solid preparations such as tablets, capsules, granules and powders can contain, generally 0.1 to 100% by weight, preferably 5 to 100% by weight of an effective ingredient.

Liquid preparations can be prepared as forms of suspensions, syrups, injections, etc. using suitable additives usually used in liquid preparations, such as water, alcohols or vegetable oils including soybean oil, peanut oil and sesame oil.

Particularly, as solvents suitable in parenteral administration including intramuscular injection, intravenous injection and subcutaneous injection, there can for example be mentioned distilled water for injection, aqueous lidocaine hydrochloride solution (for intramuscular injection), physiological saline, aqueous glucose solution, ethanol, polyethylene glycol, liquids for intravenous injection (e.g., aqeous solutions of cetric acid and sodium citrate, etc.), electrolyte solutions (for intravenous injection by drip and for intravenous injection), etc., or their mixed solutions.

These injections may include not only those wherein previous dissolution is made, but also those in the form of dissolving powder alone or with suitable additives when used. These injections usually contain 0.1 to 10% by weight, preferably 1 to 5% of an effective ingredient.

Liquid preparations such as suspensions and syrups for oral administration can contain 0.5 to 10% by weight of an effective ingredient.

It should be noted that the actually preferred dose of the compounds of the invention is varied depending on kinds of compounds used, kinds of compositions prepared, application frequency, particular sites to be treated, hosts and tumors. For example, the dose of each compound per day and per one adult is 10 to 500 mg in the case of oral administration, and 10 to 100 mg in the case of parenteral administration, preferably intravenous injection. The frequency of administration is varied depending on administration methods and symptoms, but the administration can be made in a time or in devided 2 to 5 times. Administration methods including intermittent administration such as every two-days administration or every three-days administration can also be used.

EXAMPLES

The invention is further specifically described below according to examples, but the invention is not limited to these examples.

Compounds having the following structural formulae, which were used as starting compounds, are hereinafter referred to as follows.

Compound A

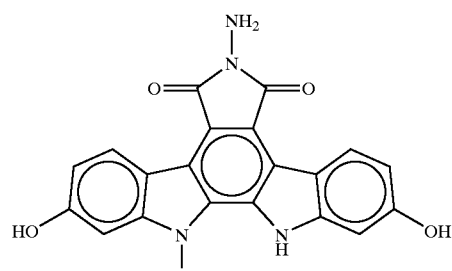

Compound B

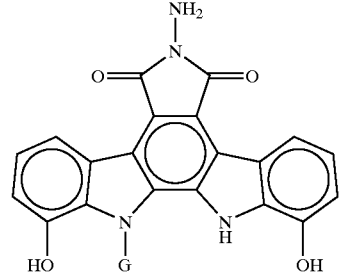

Compound C

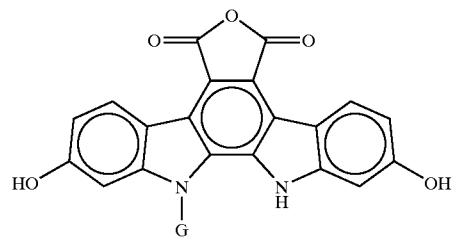

-continued

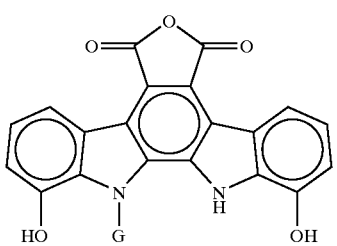

Compound D wherein, G represents a β-D-glucopyranosyl group, which is the same in the following examples.

Example 1

Compound represented by the structural formula

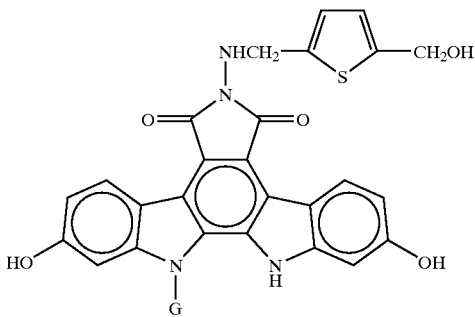

30 mg of Compound A and 30 mg of (5-t-butyldimethylsilyloxymethylthiophene)-2-carboxyaldehyde were dissolved in 6 ml of methanol, 30 ml of acetic acid was added, and the mixture was stirred at 80° C. for 4 hours. The reaction mixture was cooled to room temperature, 20 mg of sodium cyanoborohydride and 200 ml of a 10% solution of hydrochloric acid in methanol were added, and the mixture was stirred at room temperature for 30 minutes. The reaction mixture was concentrated to dryness under reduced pressure, and the residue was put on a Sephadex LH-20 column for chromatography and eluted with methanol. Fractions containing the desired compound were concentrated to dryness to obtain 27 mg of the compound represented by the above formula.

Rf value: 0.37 (Kieselgel 60F$_{254}$ made by Merck Co., developing solvent; acetonitrile:tetrahydrofuran::toluene:water:acetic acid=4:2:2:0.5:0.1)

FAB-MS(m/z):660(M$^+$)

$^1$H-NMR(300 MHz,DMSO-d$_6$, δ ppm):11.19(1H,s),9.79 (1H,s),9.75(1 H,s),8.86(1H,d,J=9.3 Hz),8.78(1H,d,J=9.0 Hz),7.17(1H,d,J=2.1 Hz),6.97(1H,d,J=2.1 Hz),6.89(1H,d,J=3.6 Hz),6.82(1H,dd,J=2.1,9.3 Hz),6.79(1H,dd,J=2.1,9.0 Hz),6.73(1H,d,J=3.3 Hz),6.10(1H,t,J=4.5 Hz),5.97(1H,d,J=8.1 Hz),5.86(1H,t,J=3.3 Hz),5.35(1H,t,J=6.0 Hz),5.32(1H,d,J=4.8 Hz),5.12(1H,d,J=4.8 Hz),4.92(1H,d,J=5.4 Hz),4.52(2H,d,J=5.7 Hz),4.40(2H,d,J=4.2 Hz),4.02(1H,m),3.91(2H,m),3.78(1H,m),3.50(2H,m)

Example 2

Compound represented by the structural formula

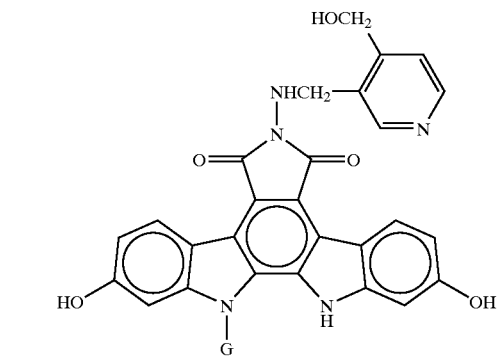

43 mg of Compound A and 100 mg of (3-t-butyldimethylsilyloxymethyl)-3-pryidinecarbaldehyde were suspended in 10 ml of methanol, 18 ml of acetic acid was added, and the mixture was stirred overnight at 80° C. The reaction mixture was concentrated, put on a Sephadex LH-20 column for chromatography and eluted with methanol. Fractions containing the desired compound were concentrated to dryness, and the residue was dissolved in 5 ml of a mixed solvent of methanol/tetrahydrofuran (1:1). 5% palladium-carbon was added and the mixture was stirred at room temperature for 3.5 hours under a hydrogen stream. The reaction mixture was filtered using Celite and the residue was dissolved in 5 ml of tetrahydrofuran. An excess amount of tetrabutylammonium fluoride (1.0 M tetrahydrofuran solution) was added and the mixture was stirred at room temperature for 30 minutes. The reaction mixture was concentrated, put on a Sephadex LH-20 column for chromatography, and eluted with methanol. Fractions containing the desired compound were concentrated to dryness to obtain 4.3 mg of the compound represented by the above formula. Rf value: 0.1 (Kieselgel 60F$_{254}$ made by Merck Co., developing solvent; acetonitrile:tetrahydrofuran::toluene:water:acetic acid=4:2:2:0.5:0.1)

FAB-MS(m/z):656(M+H)$^+$ $^1$H-NMR(300 MHz,DMSO-d$_6$, δ ppm):11.18(1H,s),9.75(1H,s),9.73(1H,s),8.84(1H,d,J=8.4 Hz),8.77(1H,d,J=8.9 Hz),8.42(1H,d,J=4.9 Hz),8.39(1H,s),7.48(1H,d,J=4.9 Hz),7.17(1H,d,J=1.1 Hz),6.97(1H,s),6.78–6.83(2H,m),609(1H,t,J=4.7 Hz),5.97(1H,d,J=6.6 Hz),5.84(1H, t,J=3.8 Hz),5.39(1H,t,J=5.8 Hz),5.30(1H,d,J=4.8 Hz),5.09(1H,d,J=4.2 Hz),4.95(2H,d,J=5.3 Hz),4.90(1H,d,J=3.3 Hz),4.27(2H,d,J=4.2 Hz),3.75–4.03(4H,m),3.47–3.52(2H,m)

Example 3

Compound represented by the structural formula

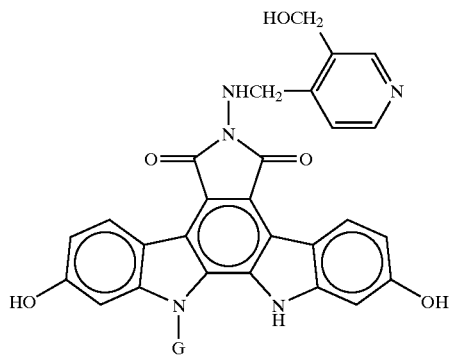

98 mg of Compound A and 92.1 mg of 4-(3-t-butoxymethyl)pyridinecarbaldehyde were dissolved in 5 ml of methanol, 18 ml of acetic acid was added, and the mixture was stirred overnight at 80° C. The reaction mixture was concentrated, and the resulting crystals were washed with chloroform and dissolved in a mixed solvent of methanol/tetrahydrofuran (1:1). 5% palladium-carbon was added and the mixture was stirred for 3 hours under a hydrogen stream. The reaction mixture was filtered using Celite and the filtrate was concentrated. The residue was dissolved in tetrahydrofuran, tetrabutylammonium fluoride was added, and the mixture was stirred at room temperature for 30 minutes. Water was added, the mixture was extracted with methyl ethyl ketone, and the organic layer was washed with an aqueous saturated sodium chloride solution and concentrated. The concentrate was put on a Sephadex LH-20 column for chromatography and eluted with methanol. Fractions containing the desired compound were concentrated to dryness to obtain 13.5 mg of the compound represented by the above formula.

Rf value: 0.10 (Kieselgel 60F$_{254}$ made by Merck Co., developing solvent; chloroform:methanol:tetrahydrofuran=2:2:1)

FAB-MS(m/z): 656(M+H)$^+$ $^1$H-NMR(300 MHz,DMSO-d$_6$, δ ppm):11.19(1H,s),9.78 (1H,s),9.75(1H,s)8.85(1H,d,J=9.1 Hz),8.77(1H,d,J=9.1 Hz), 8.51(1H,s),8.11(1H,d,J=5.1 Hz),7.59(1H,d,J=4.6 Hz),7.17 (1H,d,J=2.1 Hz),6.97(1H,d,J=1.8 Hz),6.79–6.85(2H,m), 6.25(1H,t,J=5.0 Hz),5.98(1H, d,J=8.3 Hz),5.86(1H,d,J=4.5 Hz),5.32(1H,d,J=4.5 Hz),5.23(1H,t,J=5.6 Hz),5.11(1H,d,J= 4.4 Hz),4.91(1H,d,J=4.9 Hz),4.74(2H,d,J=5.2 Hz),4.35(2H, d,J=7.8 Hz),3.73–4.05(4H,m),3.43–3.52(2H,m)

Example 4

Compound represented by the structural formula

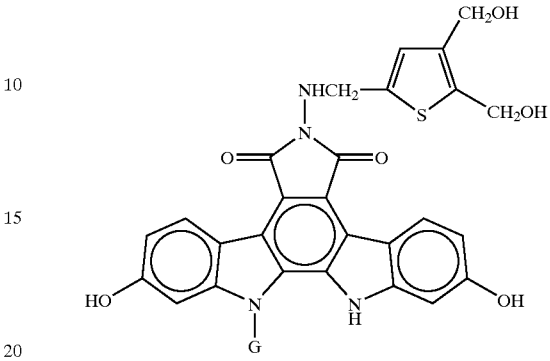

50 mg of Compound A and 100 mg of (4,5-t-butyldimethylsilyloxymethyl)thiophene-2-carboxyaldehyde were suspended in 10 ml of anhydrous methanol, 100 ml of acetic acid was added, and the mixture was stirred at 80° C. for 2 hours. The reaction mixture was put on a Sephadex LH-20 column for chromatography and eluted with methanol. Fractions containing the desired compound were concentrated to dryness to obtain 40 mg of an intermediate compound. This was suspended in 3 ml of methanol, 12 mg of sodium cyanoborohydride and and 300 ml of a 10% solution of hydrochloric acid in methanol were added, and the mixture was stirred at room temperature for 1 hour. The reaction mixture was put on a Sephadex LH-20 column for chromatography and eluted with methanol. Fractions containing the desired compound were concentrated to dryness, and the residue was purified by preparative thin layer chromatography (Kieselgel 60F$_{254}$ made by Merck Co., developing solvent; acetonitrile:tetrahydrofuran-:toluene:water:acetic acid=4:2:2:0.5:0.1) to obtain 26 mg of the compound represented by the above formula.

Rf value: 0.28 (Kieselgel 60F$_{254}$ made by Merck Co., developing solvent; acetonitrile:tetrahydrofuran-:toluene:water:acetic acid=4:2:2:0.5:0.1)

FAB-MS(m/z):690(M$^+$)

$^1$H-NMR(300 MHz,DMSO-d$_6$, δ ppm):11.17(1H,s), 9.50–10.15(2H,br),8.86(1H,d,J=8.4 Hz),8.78(1H,d,J=8.7 Hz),7.16(1H,d,J=1.8 Hz),6.97(1H,d,J=2.1 Hz),6.92(1H,s), 6.82(1H,dd,J=1.8,8.7 Hz),6.79(1H,dd,J=2.1,8.4 Hz),6.04 (1H,t,J=5.1 Hz),6.04(1H,t.J=5.1 Hz),5.96(1H,d,J=8.1 Hz), 5.88(1H,br),5.35(1H,br),5.28(1H,br),5.15(1H,br),4.93(2H, br),4.53(2H,br),4.73(2H,d,J=4.5 Hz),4.30(1H,s),4.00(1H, m),3.91(2H,m),3.77(1H,m),3.52(2H,m)

Example 5

Compound represented by the structural formula

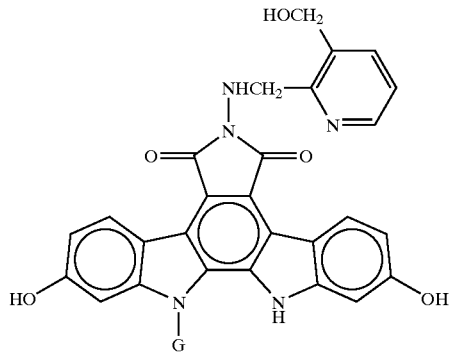

30 mg of Compound A and 50 mg of 2-(3-t-butyldimethylsilyloxymethyl) pyridinecarbaldehyde were suspended in 6 ml of methanol, 30 ml of acetic acid was added, and the mixture was stirred at 80° C. for 2 hours. The reaction mixture was put on a Sephadex LH-20 column for chromatography and eluted with methanol. Fractions containing the desired compound were concentrated to obtain 40 mg of an intermediate compound. This was dissolved in a mixed solvent of tetrahydrofuran/methanol (2:1), 15 mg of sodium cyanoborohydride and 3 ml of a solution of hydrochloric acid in methanol were added, and the mixture was stirred at room temperature for 3 hour. The reaction mixture was concentrated, put on a Sephadex LH-20 column for chromatography and eluted with methanol. Fractions containing the desired compound were concentrated to dryness to obtain 27 mg of the compound represented by the above formula.

Rf value: 0.12 (Kieselgel 60F$_{254}$ made by Merck Co., developing solvent; acetonitrile:tetrahydrofuran::toluene:water:acetic acid=4:2:2:0.5:0.1)

FAB-MS(m/z):656(M+H)$^{30}$ $^1$H-NMR(300 MHz,DMSO-d$_6$, δ ppm):11.18(1H,br),9,77(2H,br,)8.82(1H,d, J=9.0 Hz),8.784(1H,d,J=9.0 Hz),8.27(1H,dd,J=1.8,5.1 Hz),7.83(1H,d,J=8.1 Hz),7.28(1H,dd,J=8.1,5.1 Hz),7.17(1H,d,J=1.8 Hz),6.98(1H,d,J=1.8 Hz),6.82(1H,dd,J=1.8,9.1 Hz),6.79(1H,dd,J=1.8,9.0 Hz),6.15(1H,t,J=5.1 Hz),5.97(1H,d,J=8.1 Hz),5.86(1H,t,J=4.2 Hz),5.33(1H,d,J=5.4 Hz),5.31(1H,d,J=5.4 Hz),5.12(1H,d,J=4.8 Hz),4.93(1H,d,J=4.5 Hz),4.87(2H,d,J=6.0Hz),4.36(2H,d,J=5.1 Hz),4.03(1H,m),3.91(2H,s),3.79(1H,m),3.51(2H,m)

Example 6

Compound represented by the structural formula

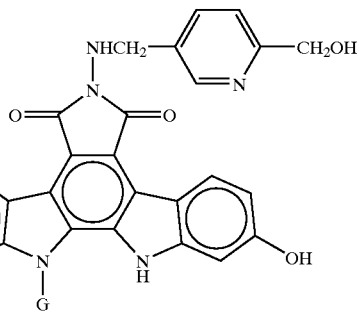

30 mg of Compound C and 65 mg of (6-hydroxymethyl-3-pyridylmethyl)hydrazine hydrochloride were dissolved in 5 ml of N,N-dimethylformamide, 0.5 ml of triethylamine was added, and the mixture was stirred at 80° C. for 3 hours. 33 mg of (6-hydroxymethyl-3-pyridylmethyl)hydrazine hydrochloride was added and the mixture was stirred at 80° C. for 2 hours. The reaction mixture was concentrated to dryness, and the residue was put on a Sephadex LH-20 column for chromatography and eluted with methanol. Fractions containing the desired compound were concentrated, and the residue was again put on a Sephadex LH-20 column for chromatography and eluted with ethanol. Fractions containing the desired compound were concentrated to dryness to obtain 7.2 mg of the compound represented by the above formula.

FAB-MS(m/z):656(M+H)$^+$ $^1$H-NMR(300 MHz,DMSO-d$_6$, δ ppm):11.12(1H,br),8.81(1H,d,J=8.7 Hz),8.73(1H,d,J=8.7 Hz),8.51(1H,s),7.90(1H,d,J=7.9 Hz),7.39(1H,d,J=7.9 Hz),7.11(1H,s),6.93(1H,s),6.77(2H,t,J=8.7 Hz),6.21(1H,t,J=3.8 Hz),5.92(1H,d,J=7.9 Hz),4.85–5.50(5H,br),4.48(2H,s),4.27(2H,d,J=3.8 Hz),3.70–4.05(4H,m),3.45–3.52(2H,m)

Example 7

Compound represented by the structural formula

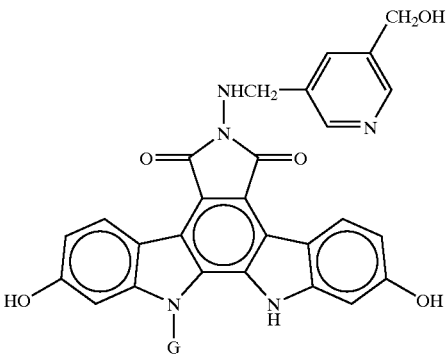

12.5 mg of Compound C and 42 mg of (5-hydroxymethyl-3-pyridylmethyl)hydrazine hydrochloride were dissolved in 1 ml of N,N-dimethylformamide, 0.1 ml of triethylamine was added, and the mixture was stirred at 80° C. for 2.5 hours. 0.1 ml of triethylamine was added and the mixture was stirred overnight at 50° C. The reaction mixture was concentrated to dryness, and the residue was put on a Sephadex LH-20 column for chromatography and eluted with methanol. Fractions containing the desired compound were concentrated, and the residue was again put on a Sephadex LH-20 column for chromatography and eluted with ethanol. Fractions containing the desired compound were concentrated to dryness to obtain 2.4 mg of the compound represented by the above formula.

Rf value: 0.18 (Kieselgel 60F$_{254}$ made by Merck Co., developing solvent; acetonitrile:tetrahydrofuran::toluene:water:acetic acid=4:2:2:0.5:0.1)

FAB-MS(m/z):656(M+H)$^+$ $^1$H-NMR(300 MHz,DMSO-d$_6$, δ ppm):11.18(1H,br), 9.60–10.02(2H,br),8.84(1H,d,J=8.5 Hz),8.76(1H,d,J=8.6 Hz),8.55(1H,s),8.37(1H,s),7.84(1H,s),7.16(1H,s),7.00(1H, s),6.75–6.85(2H,m),6.21(1H,t,J=4.7 Hz),5.95(1H,d,J=7.8 Hz),5.88–5.95(1H,br),5.40–5.48(1H,br),5.26–5.35(1H,br), 5.15–5.25(1H,br),4.90–4.93(1H,br),4.56(2H,d,J=4.7 Hz), 4.50(2H, s),3.72–4.05(4H,m),3.45–3.55(2H,m)

Example 8

Compound represented by the structural formula

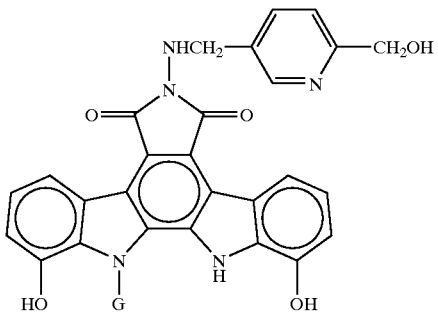

30 mg of Compound D and 65 mg of (6-hydroxymethyl-3-pyridylmethyl)hydrazine hydrochloride were dissolved in 5 ml of N,N-dimethylformamide, 0.5 ml of triethylamine was added, and the mixture was stirred at 80° C. for 1.5 hours. The reaction mixture was dried and concentrated, and the residue was put on a Sephadex LH-20 column for chromatography and eluted with methanol. Fractions containing the desired compound were concentrated to dryness to obtain 29 mg of the compound represented by the above formula.

FAB-MS(m/z):656(M+H)$^+$ $^1$H-NMR(300 MHz,DMSO-d$_6$, δ ppm):10.89(1H,br), 10.36(1H,br),9.97(1 H,br),8.67(1H,d,J=7.9 Hz),8.52(1H,d, J=2.2 Hz),8.50(1H,d,J=7.9 Hz),7.93(1H,dd,J=2.2,8.1 Hz), 7.41(1H,d,J=8.1 Hz),7.18(2H,t,J=7.9 Hz),7.02(1H,d,J=7.9 Hz),7.00(2H,t,J=7.9 Hz),6.29(1H,t,J=4.5 Hz),5.42(1H,d,J= 5.6 Hz),5.33(1H,d,J=6.1 Hz),5.32(1H,t,J=6.0 Hz),5.21(1H, d,J=5.3 Hz),4.82–4.91(1H,br),4.48(2H,d,J=6.0 Hz),4.29 (2H,d,J=4.5 Hz),3.91–4.12(2H,m),3.52–3.79(3H,m), 3.30–3.40(1H,m)

Example 9

Compound represented by the structural formula

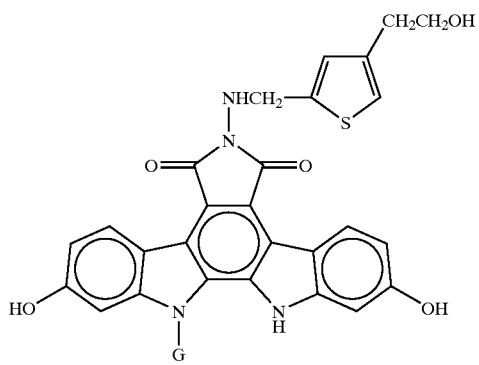

30 mg of Compound B and 152 mg of 4-(t-butyldimethylsilyloxyethyl)thiophene-2-carbaldehyde were suspended in 6 ml of anhydrous methanol, 30 ml of acetic acid was added, and the mixture was stirred at 80° C. for 2 hours. The reaction mixture was put on a Sephadex LH-20 column for chromatography and eluted with methanol. Fractions containing the desired compound were concentrated to dryness to obtain 31 mg of an intermediate compound. This was suspended in 3 ml of methanol, 30 mg of sodium cyanoborohydride and 300 ml of a 10% solution of hydrochloric acid in methanol were added, and the mixture was stirred at room temperature for 1 hour. The reaction mixture was diluted with ethyl acetate, washed with water and an aqueous saturated sodium chloride solution, dried and concentrated. The residue was put on a Sephadex LH-20 column for chromatography and eluted with methanol. Fractions containing the desired compound were concentrated to dryness to obtain 5 mg of the compound represented by the above formula.

Rf value: 0.43 (made by Merck Co., toluene:water:acetic acid=4:2:2:0.5:0.1)

FAB-MS(m/z):675(M)$^+$ $^1$H-NMR(300 MHz,DMSO-d$_6$, δ ppm):11.19(1H,s),9.80 (2H,br),8.86(1H,d,J=9.0 Hz),8.78(1 H,d,J=8.7 Hz),7.17(1H, d,J=1.8 Hz),7.03(1H,s),6.98(1H,d,J=2.1 Hz),6.95(1H,s), 6.80(2H,dt,J=2.1,8.7 Hz),6.08(1H,t,J=5.1 Hz),5.96(1H,d,J= 7.8 Hz),5.89(1H,br),5.36(1H,br),5.13(1H,br),4.93(1H,br), 4.57(1H,br),4.38(2H,d,J=4.2 Hz),4.05(2H,m),3.92(2H,s), 3.77(1H,m),3.50(5H,m)

Example 10

Compound represented by the structural formula

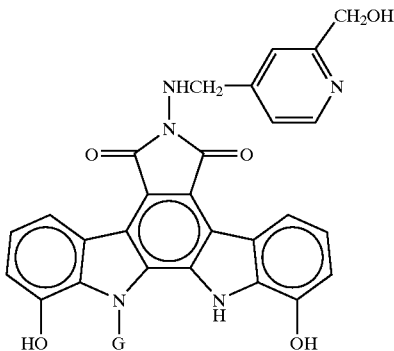

17 mg of Compound D and 12 mg of 4-(2-hydroxymethyl-4-pyridylmethyl)hydrazine trifluoroacetate were dissolved in 2 ml of N,N-dimethylformamide, 0.1 ml of triethylamine was added, and the mixture was stirred at 75° C. for 2 hours. Water and ethyl acetate were added to the reaction mixture, and the mixture was extracted three times with water. Sodium chloride was added to the aqueous layer and the mixture was extracted three times with methyl ethyl ketone. The organic layer was dried and concentrated, and the residue was put on a Sephadex LH-20 column for chromatography and eluted with methanol. Fractions containing the desired compound were concentrated to dryness to obtain 8 mg of the compound represented by the above formula.

FAB-MS(m/z):656(M+H)$^+$ $^1$H-NMR(300 MHz,DMSO-d$_6$, δ ppm):10.90(1H,br),8.66 (1H,d,J=7.6 Hz),8.50(1H,d,J=7.6 Hz),8.41(1H,d,J=5.0 Hz), 7.57(1H,s),7.48(1H,d,J=5.0 Hz),7.17(2H,t,J=7.6 Hz),7.07 (1H,d,J=7.6 Hz),7.00(1H,d,J=7.6 Hz),6.98(1H,t,J=7.6 Hz), 6.32(1H,t,J=4.8 Hz),5.36(1H,t,J=3.7 Hz),5.10–5.50(4H,br), 4.51(2H,d,J=3.7 Hz),4.34(2H,d,J=4.8 Hz),3.91–4.12(2H, m),3.51–3.80(3H,m)

Example 11

Compound represented by the structural formula

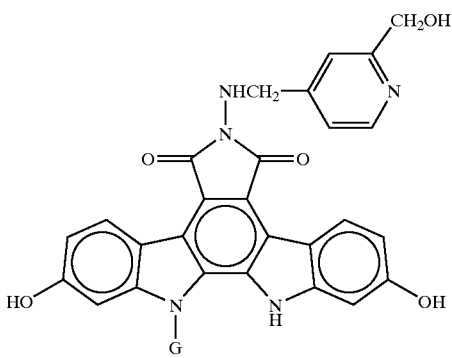

17 mg of Compound C and 12 mg of (2-hydroxymethyl-4-pyridylmethyl)hydrazine trifluoroacetate were dissolved in 1 ml of N,N-dimethylformamide, 0.1 ml of triethylamine was added, and the mixture was stirred at 80° C. for 3.5 hours. Water and ethyl acetate were added to the reaction mixture, and the mixture was separated into two layers. Sodium chloride was added to the aqueous layer and the mixture was extracted with methyl ethyl ketone. The organic layer was dried and concentrated, and the residue was put on a Sephadex LH-20 column for chromatography and eluted with methanol. Fractions containing the desired compound were concentrated to dryness to obtain 4 mg of the compound represented by the above formula.

FAB-MS(m/z):656(M+H$^+$)

$^1$H-NMR(300 MHz,DMSO-d$_6$, δ ppm):11.17(1H,br), 9.55–10.05(2H,br),8.85(1H,d,J=8.4 Hz),8.77(1H,d,J=8.2 Hz),8.41(1H,d,J=5.1 Hz),7.56(1H,s),7.47(1H,d,J=5.1 Hz), 7.15(1H,s),6.96(1H,s),6.72–6.85(2H,m),6.26(1H,t,J=4.9 Hz),5.94(1H,d,J=8.6 Hz),5.80–5.99(1H,br),5.30–5.42(2H, br),5.10–5.20(1H,br),4.85–4.95(1H,br),4.51(2H,d,J=1.8 Hz),4.32(2H,d,J=4.5 Hz),3.89–4.04(1H,m),3.90(2H,m), 3.74–3.78(1H,m),3.50(2H,m)

Example 12

Compound represented by the structural formula

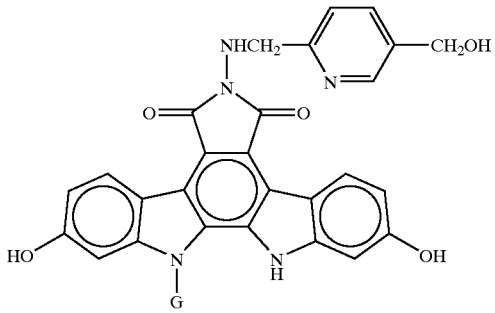

14 mg of Compound A and 14.7 mg of 5-t-butyldimethylsilyloxymethylpyridine-2-carbaldehyde were suspended in 2 ml of anhydrous methanol, 8 ml of acetic acid was added, and the mixture was stirred overnight at 80° C. The reaction mixture was put on a Sephadex LH-20 column for chromatography and eluted with methanol. Fractions containing the desired compound were concentrated to dryness to obtain 15.3 mg of an intermediate compound. 75 mg of sodium cyanoborohydride was suspended in 1 ml of tetrahydrofuran, and 0.55 ml of zinc chloride (1.0 M diethyl ether solution) was added dropwise. A suspension of 15.3 mg of the intermediate compound in 3 ml of tetrahydrofuran was added, and the mixture was stirred at room temperature for 2.5 hours. An aqueous saturated sodium bicarbonate solution was added to the reaction mixture, and the mixture was extracted with methyl ethyl ketone. The organic layer was dried and concentrated, the residue was dissolved in 3 ml of tetrahydrofuran, and an excess amount of tetrabutylammonium fluoride (1 M tetrahydrofuran solution) was added dropwise at 0° C. The mixture was stirred at room temperature for 30 minutes, water was added, and the mixture was extracted with methyl ethyl ketone. The organic layer was dried and concentrated, and the residue was put on a Sephadex LH-20 column for chromatography and eluted with methanol. Fractions containing the desired compound were concentrated to dryness to obtain 4.5 mg of the compound represented by the above formula.

Rf value: 0.1 (Kieselgel 60F$_{254}$ made by Merck Co., developing solvent; chloroform:methanol:tetrahydrofuran= 3:1:1)

FAB-MS(m/z):656(M+H)$^+$ $^1$H-NMR(300 MHz,DMSO-d$_6$, δ ppm):11.18(1H,s),9.77 (2H,br),8.84(1H,d,J=8.5 Hz),8.76(1H,d,J=8.6 Hz),8.35(1H, d,J=1.7 Hz),7.72(2H,s),7.17(1H,d,J=1.7 Hz),6.98(1H,d,J=

1.9 Hz),6.78–6.98(2H,m),6.22(1H,t,J=4.6 Hz),5.96(1H,d,J= 8.9 Hz),5.87(1H,br),5.35(1H,br),5.22(1H,t,J=2.0 Hz),5.11 (1H,br),4.91(1H,br),4.46(2H,d,J=4.2 Hz),4.35(2H,d,J=4.6 Hz),3.73–4.09(4H,m),3.49(2H, s)

Example 13

Compound represented by the structural formula

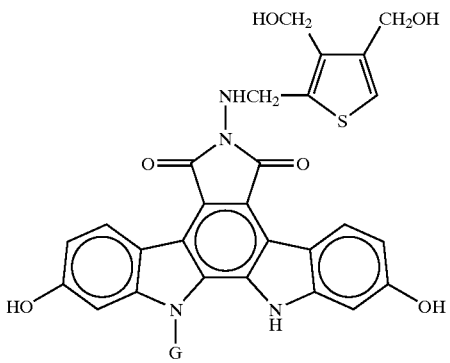

30 mg of Compound A and 30 mg of 3,4-bis-(t-butyldimethylsilyloxymethyl) thiophene-2-carbaldehyde were suspended in 6 ml of anhydrous methanol, 30 ml of acetic acid was added, and the mixture was stirred at 80° C. for 2 hours. The reaction mixture was put on a Sephadex LH-20 column for chromatography and eluted with methanol. Fractions containing the desired compound were concentrated to dryness to obtain 31 mg of an intermediate compound. This was suspended in 5 ml of methanol, 10 mg of sodium cyanoborohydride and 100 ml of a 10% solution of hydrochloric acid in methanol were added, and the mixture was stirred at room temperature for 30 minutes. The reaction mixture was diluted with ethyl acetate, and washed with water and an aqueous saturated sodium chloride solution. The organic layer was dried and concentrated, and the residue was put on a Sephadex LH-20 column for chromatography and eluted with methanol. Fractions containing the desired compound were concentrated to dryness to obtain 25 mg of the compound represented by the above formula.

Rf value: 0.30 (Kieselgel 60F$_{254}$ made by Merck Co., developing solvent; acetonitrile: tetrahydrofuran:toluene:water:acetic acid=4:2:2:0.5:0.1)

FAB-MS(m/z):691(M+H)$^+$ $^1$H-NMR(300 MHz,DMSO-d$_6$, δ ppm):11.19(1H,s),9.79 (1H,s),9.76(1H,s),8.86(1H,d,J=8.4 Hz),8.78(1H,d,J=8.7 Hz),7.18(1H,d,J=1.8 Hz),7.15(1H,s),6.98(1H,d,J=2.1 Hz), 6.82(2H,dt,J=8.7,1.8 Hz),6.04(1H,t,J=5.4 Hz),5.97(1H,d,J= 8.1 Hz),5.86(1H,t,J=3.6 Hz),5.33(1H,d,J=4.2 Hz),5.12(1H, d,J=4.2 Hz),5.01(1H,t,J=6.0 Hz),4.93(1H,d,J=4.8 Hz),4.85 (1H,t,J=5.7 Hz),4.52(2H,d,J=5.7 Hz),4.70(2H,d,J=5.7 Hz), 4.40(2H,d,J=4.8 Hz),4.01(1H,m),3.92(2H,m),3.77(1H,m), 3.50(2H,m)

Example 14

Compound represented by the structural formula

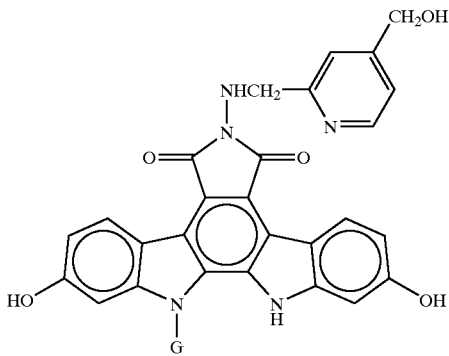

18 mg of Compound A and 7 mg of 4-hydroxymethylpyridine-2-carbaldehyde were suspended in 2 ml of anhydrous methanol, several drops of acetic acid were added, and the mixture was stirred at 80° C. for 1.5 hours. The reaction mixture was concentrated to dryness, and the residue was put on a Sephadex LH-20 column for chromatography and eluted with methanol. Fractions containing the desired compound were concentrated to dryness to obtain 22 mg of an intermediate compound. 90 mg of sodium cyanoborohydride was suspended in 1 ml of tetrahydrofuran, and 0.66 ml of zinc chloride (1.0 M diethyl ether solution) was added dropwise. A suspension of 22 mg of the intermediate compound in 3 ml of tetrahydrofuran was added, and the mixture was stirred at room temperature for 2.5 hours. Water was added to the reaction mixture, and the mixture was made weakly alkaline with an aqueous saturated sodium bicarbonate solution and extracted with ethyl acetate. The organic layer was dried and concentrated, and the residue was put on a Sephadex LH-20 column for chromatography and eluted with methanol. Fractions containing the desired compound were concentrated to dryness to obtain 11 mg of the compound represented by the above formula.

FAB-MS(m/z):656(M+H)$^+$ $^1$H-NMR(300 MHz,DMSO-d$_6$, δ ppm):11.21(1H,s),9.80 (1H,s),9.77(1H,s),8.86(1H,d,J=8.6 Hz),8.78(1H,d,J=8.1 Hz),7.82–7.95(1H,m),7.68–7.75(1H,m),7.33–7.43(1H,m), 7.19(1H,s),7.00(1H,s),6.78–6.89(2H,m),6.22(1H,t,J=4.5 Hz),5.97(1H,d,J=7.9 Hz),5.86(1H,t,J=3.8 Hz),5.33(1H,d,J= 4.2 Hz),5.29(1H,t,J=5.9 Hz),5.11(1H,d,J=5.0 Hz),4.91(1H, d,J=4.1 Hz),4.42(2H,d,J=5.5 Hz),4.33(2H,d,J=1.6 Hz), 3.99–4.09(1H,m),3.91(2H,m),3.72–3.80(1H,m),3.50(2H,m)

Example 15

Compound represented by the structural formula

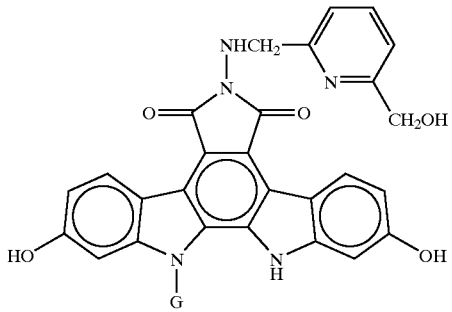

15 mg of Compound A and 6.9 mg of 6-hydroxymethylpyridine-2-carbaldehyde were suspended in 1 ml of anhydrous methanol, several drops of acetic acid were added, and the mixture was stirred at 80° C. for 5 hours. The reaction mixture was concentrated to dryness, and the residue was put on a Sephadex LH-20 column for chromatography and eluted with methanol. Fractions containing the desired compound were concentrated to dryness to obtain 5.2 mg of an intermediate compound. 68 mg of sodium cyanoborohydride was suspended in 2 ml of tetrahydrofuran, and 0.5 ml of zinc chloride (1.0 M diethyl ether solution) was added dropwise. A suspension of 5.2 mg of the intermediate compound in 1 ml of tetrahydrofuran was added, and the mixture was stirred overnight at room temperature. Water was added to the reaction mixture, and the mixture was made weakly alkaline with an aqueous saturated sodium bicarbonate solution and extracted with ethyl acetate. The organic layer was dried and concentrated, and the residue was put on a Sephadex LH-20 column for chromatography and eluted with methanol. Fractions containing the desired compound were concentrated to dryness to obtain 2.0 mg of the compound represented by the above formula.

Rf value: 0.29 (Kieselgel 60F$_{254}$ made by Merck Co., developing solvent: acetonitrile:tetrahydrofuran:toluene:water:acetic acid=4:2:2:0.5:0.1)

FAB-MS(m/z):656(M+H$^+$)

$^1$H-NMR(300 MHz,DMSO-d$_6$, δ ppm):11.21(1H,s),9.80 (1H,s),9.77(1H,s),8.86(1H,d,J=8.6 Hz),8.78(1H,d,J=8.1 Hz),7.82–7.95(1H,m),7.68–7.75(1H,m),7.33–7.43(1H,m), 7.19(1H,s),7.00(1H,s),6.78–6.89(2H,m),6.22(1H,t,J=4.5 Hz),5.97(1H,d,J=7.9 Hz),5.86(1H,t,J=3.8 Hz),5.33(1H,d,J= 4.2 Hz),5.29(1H,t,J=5.9 Hz),5.11(1H,d,J=5.0 Hz),4.91(1H, d,J=4.1 Hz),4.42(2H,d,J=5.5 Hz),4.33(2H,d,J=1.6 Hz), 3.99–4.09(1H,m),3.91(2H,m),3.72–3.80(1H,m),3.50(2H,m)

Example 16

Compound represented by the structural formula

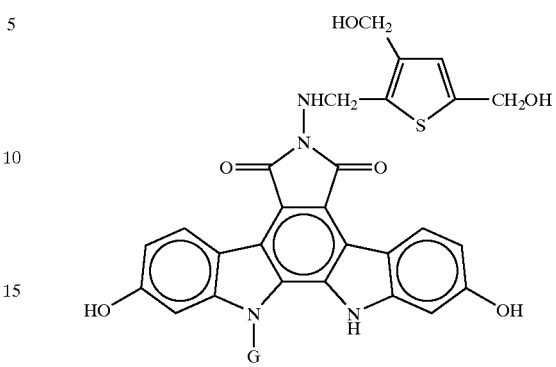

40 mg of Compound A and 60 mg of 3,5-bis-(t-butyldimethylsilyloxymethyl)thiophene-2-carbaldehyde were suspended in 8 ml of anhydrous methanol, 40 ml of acetic acid was added, and the mixture was stirred at 80° C. for 2 hours. The reaction mixture was put on a Sephadex LH-20 column for chromatography and eluted with methanol. Fractions containing the desired compound were concentrated to dryness to obtain 46 mg of an intermediate compound. This was suspended in 5 ml of methanol, 30 mg of sodium cyanoborohydride and 300 ml of a 10% solution of hydrochloric acid in methanol were added, and the mixture was stirred at room temperature for 30 minutes. The reaction mixture was diluted with ethyl acetate, and washed with water and an aqueous saturated sodium chloride solution. The organic layer was dried and concentrated, and the residue was put on a Sephadex LH-20 column for chromatography and eluted with methanol. Fractions containing the desired compound were concentrated to dryness to obtain 36 mg of the compound represented by the above formula.

Rf value: 0.24 (Kieselgel 60F$_{254}$ made by Merck Co., developing solvent: acetonitrile:tetrahydrofuran:toluene:water:acetic acid=4:2:2:0.5:0.1)

FAB-MS(m/z):690(M)$^+$ $^1$H-NMR(300 MHz,DMSO-d$_6$, δ ppm):11.19(1H,s),9.79 (1H,s),9.76(1H,s),8.86(1H,d,J=8.4 Hz),8.78(1H,d,J=8.4 Hz),7.18(1H,d,J=1.8 Hz),6.98(1H,d,J=1.8 Hz),6.83(1H,s), 6.82(2H,dt,J=1.8,8.4 Hz),5.99(1H,t,J=4.8 Hz),5.97(1H,d,J= 9.0 Hz),5.87(1H,t,J=4.2 Hz),5.35(1H,d,J=5.2 Hz),5.33(1H, t,J=4.8 Hz),5.12(1H,d,J=5.1 Hz),4.96(1H,d,J=5.7 Hz),4.94 (1H,d,J=5.4 Hz),4.49(4H,d,J=6.6 Hz),4.34(2H,d,J=4.8 Hz), 4.03(1H,m),3.92(2H,m),3.77(1H,m),3.50(2H,m)

Example 17

Compound represented by the structural formula

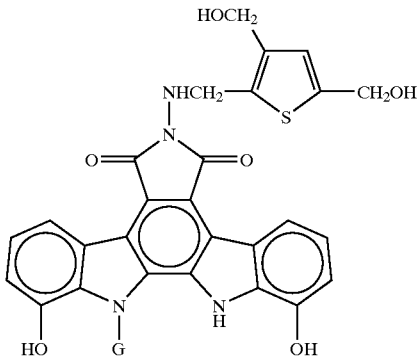

50 mg of Compound B and 60 mg of 3,5-bis-(t-butyldimethylsilyloxymethyl)thiophene-2-carbaldehyde were dissolved in 12 ml of anhydrous methanol/N,N-dimethylformamide (5:1), 50 ml of acetic acid was added, and the mixture was stirred overnight at 80° C. The reaction mixture was diluted with ethyl acetate, washed with water and an aqueous saturated sodium chloride solution, dried, and concentrated. The residue was put on a Sephadex LH-20 column for chromatography and eluted with methanol. Fractions containing the desired compound were concentrated to dryness, and the residue was dissolved in 6 ml of a mixed solvent of tetrahydrofuran/methanol (2:1). 30 mg of sodium cyanoborohydride and 300 ml of a 10% solution of hydrochloric acid in methanol were added, and the mixture was at room temperature for 1 hour. The reaction mixture was diluted with ethyl acetate, and washed with an aqueous saturated sodium bicarbonate solution and an aqueous saturated sodium chloride solution. The organic layer was dried and concentrated, and the residue was put on a Sephadex LH-20 column for chromatography and eluted with methanol. Fractions containing the desired compound were concentrated to dryness to obtain 37 mg of the compound represented by the above formula.

Rf value: 0.31 (Kieselgel 60F$_{254}$ made by Merck Co., developing solvent: acetonitrile:tetrahydrofuran:toluene:water:acetic acid=4:2:2:0.5:0.1)

FAB-MS(m/z):690(M)$^+$ $^1$H-NMR(300 MHz,DMSO-d$_6$, δ ppm):10.90(1H,s),10.37(1H,s),9.98(1H,br),8.69(1H,d,J=8.4 Hz),8.52(1H,d,J=8.4 Hz),7.19(1H,d,J=1.5,8.4 Hz),7.04(1H,d,J32 8.6Hz),7.01(2H,t,J=8.4 Hz),6.83(1H,s),6.04(1H,t,J=4.8 Hz),5.42(1H,d,J=5.7 Hz),5.35(2H,d,J=6.0 Hz),5.21(1H,d,J=5.4 Hz),4.95(1H,t,J=6.0 Hz),4.91(1H,br),4.50(4H,t,J=5.7 Hz),4.36(2H,d,J=5.4Hz),4.00(2H,m),3.73(1H,m),3.62(2H,m),3.40(1H,m)

Example 18

Compound represented by the structural formula

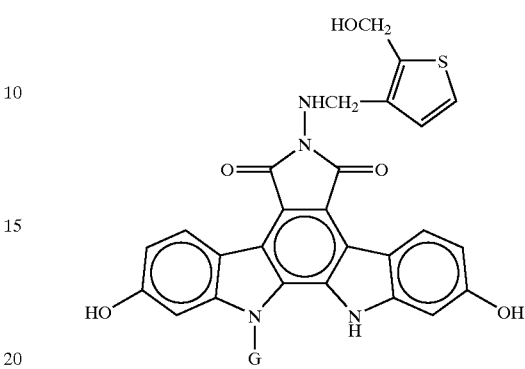

20 mg of Compound A and 20 mg of 2-hydroxymethylthiophene-3-carbaldehyde were dissolved in 4 ml of anhydrous methanol, 20 ml of acetic acid was added, and the mixture was stirred at 80° C. for 2 hours. The reaction mixture was concentrated under reduced pressure, and the residue was put on a Sephadex LH-20 column for chromatography and eluted with methanol. Fractions containing the desired compound were concentrated to dryness, and the residue was dissolved in 3 ml of a mixed solvent of tetrahydrofuran/methanol (2:1). 30 mg of sodium cyanoborohydride and 300 ml of a 10% solution of hydrochloric acid in methanol were added, and the mixture was stirred at room temperature for 30 minutes. The reaction mixture was concentrated under reduced pressure, and the residue was put on a Sephadex LH-20 column for chromatography and eluted with methanol. Fractions containing the desired compound were concentrated to dryness to obtain 16 mg of the compound represented by the above formula.

Rf value: 0.49 (Kieselgel 60F$_{254}$ made by Merck Co., developing solvent: acetonitrile:tetrahydrofuran:toluene:water:acetic acid=4:2:2:0.5:0.1)

FAB-MS(m/z):660(M)$^+$ $^1$H-NMR(300 MHz,DMSO-d$_6$, δ ppm):11.18(1H,s),9.79(1H,s),9.75(1H,s),8.86(1H,d,J=8.4 Hz),8.78(1H,d,J=8.4 Hz),7.30(1H,d,J=4.8 Hz),7.17(1H,d,J=2.1Hz),7.09(1H,t,J=5.4 Hz),6.98(1H,d,J=2.1 Hz),6.82(1H,dd,J=2.1,8.4 Hz),6.80(1H,dd,J=2.1,8.4 Hz),5.97(1H,d,J=8.1 Hz),5.92(1H,t,J=5.1 Hz),5.86(1H,t,J=3.9 Hz),5.37(1H,d,J=5.7Hz),5.33(1H,d,J=4.5 Hz),5.12(1H,d,J=4.8 Hz),4.93(1H,d,J=4.8 Hz),4.76(2H,d,J=5.7 Hz),4.20(2H,d,J=5.1 Hz),4.00(1H,m),3.91(2H,s),3.77(1H,m),3.50(2H,m)

Example 19

Compound represented by the structural formula

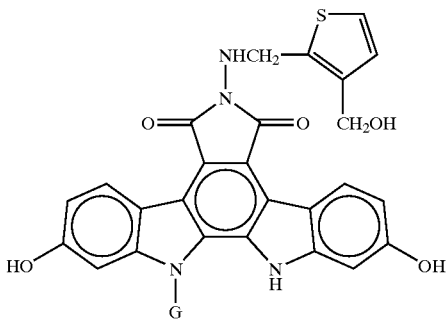

30 mg of Compound A and 30 mg of 3-t-butyldimethylsilyloxymethylthiophene-2-carbaldehyde were dissolved in 5 ml of anhydrous methanol, 30 ml of acetic acid was added, and the mixture was stirred 80° C. for 2 hours. The reaction mixture was concentrated under reduced pressure, and the residue was put on a Sephadex LH-20 column for chromatography and eluted with methanol. Fractions containing the desired compound were concentrated to dryness, and the residue was suspended in 3 ml of methanol. 30 mg of sodium cyanoborohydride and 300 ml of a 10% solution of hydrochloric acid in methanol were added, and the mixture was stirred at room temperature for 1 hours. The reaction mixture was put on a Sephadex LH-20 column for chromatography and eluted with methanol. Fractions containing the desired compound were concentrated to dryness to obtain 24 mg of the compound represented by the above formula.

Rf value: 0.40 (Kieselgel 60$F_{254}$ made by Merck Co., developing solvent: acetonitrile:tetrahydrofuran-:toluene:water:acetic acid=4:2:2:0.5:0.1)

FAB-MS(m/z):660(M)$^+$ $^1$H-NMR(300 MHz,DMSO-$d_6$, δ ppm):11.19(1H,s),9.78 (1H,s),9.75(1H,s),8.85(1H,d,J=8.7 Hz),8.78(1H,d,J=9.0 Hz),7.31(1H,d,J=4.8 Hz),7.18(1H,d,J=1.8 Hz),699(1H,d,J= 4.8 Hz),6.97(1H,d,J=1.8 Hz),6.81 (2H,dd,J=1.8,9.0 Hz), 6.06(1H,t,J=4.8 Hz),5.97(1H,d,J=8.7 Hz),5.86(1H,t,J=3.9 Hz),5.33(1H,d,J=4.5 Hz),5.12(1H,d,J=4.5 Hz),4.99(1H,t,J= 5.4 Hz),4.93(1H,d,J=5.1 Hz),4.53(2H,d,J=5.7 Hz),4.38(2H, d,J=4.8 Hz),4.02(1H,m),3.91(2H,m),3.77(1H,m),3.50(2H, m)

Example 20

Compound represented by the structural formula

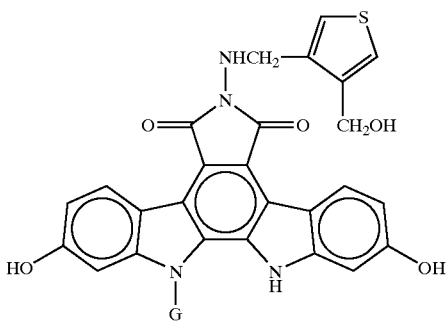

30 mg of Compound A and 30 mg of 4-t-butyldimethylsilyloxythiophene-3-carbaldehyde were suspended in 6 ml of methanol, 30 ml of acetic acid was added, and the mixture was stirred 80° C. for 2 hours. The reaction mixture was put on a Sephadex LH-20 column for chromatography and eluted with methanol. Fractions containing the desired compound-were concentrated to dryness, and the residue was dissolved in 5 ml of a mixed slovent of tetrahydrofuran/methanol (2:1). 20 mg of sodium cyanoborohydride and 200 ml of a 10% solution of hydrochloric acid in methanol were added, and the mixture was stirred at room temperature for 30 minutes. The reaction mixture was diluted with ethyl acetate, washed with water and an aqueous saturated sodium chloride solution, dried and concentrated. The residue was put on a Sephadex LH-20 column for chromatography and eluted with methanol. Fractions containing the desired compound were concentrated to dryness to obtain 15 mg of the compound represented by the above formula.

Rf value: 0.47 (Kieselgel 60$F_{254}$ made by Merck Co., developing solvent: acetonitrile:tetrahydrofuran-:toluene:water:acetic acid=4:2:2:0.5:0.1)

FAB-MS(m/z):661 (M+H)$^+$ $^1$H-NMR(300 MHz,DMSO-$d_6$, δ ppm):11.19(1H,s),9.79 (1H,s),9.76(1H,s),8.86(1H,d,J=8.7 Hz),8.78(1H,d,J=8.7 Hz),7.43(1H,d,J=3.3 Hz),7.30(1H,d,J=3.6 Hz),7.17(1H,d,J= 2.1 Hz),6.98(1H,d,J=2.1 Hz),6.83(1H,dd,J=2.1,8.7 Hz),6.81 (1H,dd,J=2.1,8.7 Hz),6.04(1H,t,J=5.1 Hz),5.97(1H,d,J=9.0 Hz),5.87(1H,t,J=3.6 Hz),5.34(1H,d,J=3.9 Hz),5.12(1H,d,J= 5.1 Hz),5.10(1H,t,J=5.1 Hz),4.92(1H,d,J=4.5 Hz),4.67(2H, d,J=5.4 Hz),4.23(2H,d,J=4.2 Hz),4.01(1H,m),3.92(2H,s), 3.77(1H,m),3.50(2H,m)

Example 21

Compound represented by the structural formula

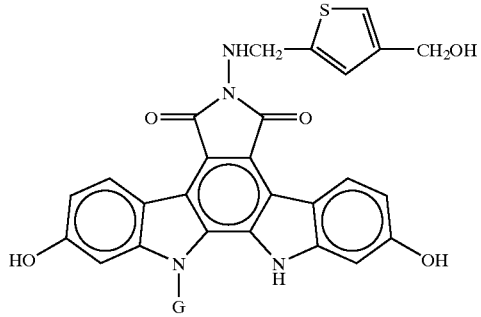

38 mg of Compound A and 25 mg of 4-hydroxymethylthiophene-2-carbaldehyde were suspended in 7 ml of anhydrous methanol, 45 ml of acetic acid was added, and the mixture was stirred at 80° C. for 7 hours. The reaction mixture was concentrated under reduced pressure, and 38 mg of crystals obtained by filtration from methanol/chloroform. The crystals were dissolved in 10 ml of tetrahydrofuran/methanol (4:1), 13 mg of sodium cyanoborohydride and 0.5 ml of a 10% solution of hydrochloric acid in methanol were added, and the mixture was stirred at room temperature for 30 minutes. The reaction mixture was diluted with ethyl acetate, washed with an aqueous saturated sodium chloride solution, dried and concentrated. The residue was put on a Sephadex LH-20 column for chromatography and eluted with methanol. Fractions containing the desired compound were concentrated to dryness to obtain 21.7 mg of the compound represented by the above formula.

Rf value: 0.24 (Kieselgel 60$F_{254}$ made by Merck Co., developing solvent: acetonitrile:tetrahydrofuran-:toluene:water:acetic acid=4:2:2:0.5:0.1)

FAB-MS(m/z):660(M⁺)

¹H-NMR(300 MHz,DMSO-d₆, δ ppm):11.19(1H,s),9.77 (2H,br),8.86(1H,d,J=8.6 Hz),8.78(1H,d,J=8.6 Hz),7.17(1H, s),7.14(1H,d,J=1.8 Hz),6.98(2H,m),6.81(1H,dt,J=18.,6.9 Hz),6.12(1H,t,J=5.1 Hz),5.97(1H,d,J=8.1 Hz),5.87(1H,s), 5.35(1H,d,J=1.8 Hz),5.13(1H,d,J=2.4 Hz),5.01 (1H,t,J=5.4 Hz),4.93(1H,d,J=3.6 Hz),4.40(2H,d,J=4.5 Hz),4.34(2H,d,J= 4.8 Hz),4.00(1H,dd,J=2.1,11.6 Hz),3.91(2H,s),3.79(1H,m), 3.51 (2H,br)

Example 22

Compound represented by the structural formula

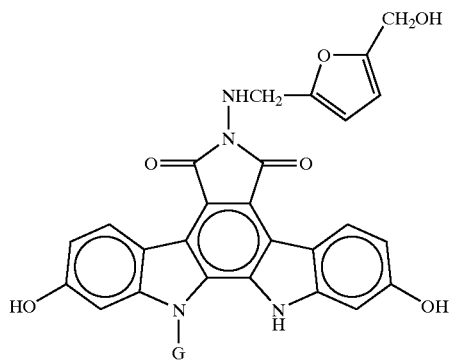

107 mg of Compound A and 126 mg of 5-hydroxymethylfurfural were suspended in 2 ml of methanol, several drops of acetic acid were added, and the mixture was stirred overnight at 80° C. The reaction mixture was concentrated and the obtained solid was washed with chloroform. The solid was dissolved in 5 ml of a mixed solvent of methanol/tetrahydrofuran (1:2), 62.8 mg of sodium cyanoborohydride and 5 ml of a 10% solution of hydrochloric acid in methanol were added, and the mixture was stirred at room temperature for 30 minutes. The reaction mixture was diluted with a mixed slovent of ethyl acetate/ methyl ethyl ketone, and washed with water and an aqueous saturated sodium chloride solution. The organic layer was dried, concentrated, put on a Sephadex LH-20 column for chromatography and eluted with methanol. Fractions containing the desired compound were concentrated to dryness to obtain 103 mg of the compound represented by the above formula.

FAB-MS(m/z):644(M)⁺

¹H-NMR(300 MHz,DMSO-d₆, δ ppm):11.19(1H,s),9.77 (2H,br),8.85(1H,d,J=8.5 Hz),8.77(1H,d,J=8.6 Hz),7.18(1H, d,J=2.1 Hz),6.98(1H,d,J=1.7 Hz),6.75–6.86(2H,m),6.31 (1H,d,J=3.1 Hz),6.15(1H,d,J=3.1 Hz),6.03(1H,t,J=4.7 Hz), 5.97(1H,d,J=8.3 Hz),5.87(1H,t,J=3.6 Hz),5.34(1H,d,J=3.9 Hz),5.08–5.15(2H,m),4.93(1H,d,J=4.5 Hz), 4.28(2H,d,J= 5.6 Hz),4.20(2H,d,J=4.7 Hz),3.72–4.05(4H,m),3.45–3.55 (2H,m)

Example 23

Compound represented by the structural formula

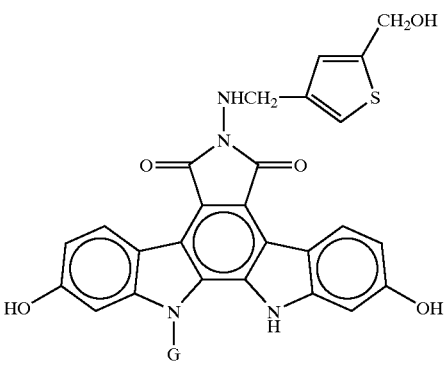

40 mg of Compound A and 40 mg of 5-hydroxymethylthiophene-3-carbaldehyde were suspended in 8 ml of methanol, 40 ml of acetic acid was added, and the mixture was stirred at 80° C. for 3 hours. The reaction mixture was cooled to room temperature, chloroform was added, and the resulting powder was obtained by filtration. This was suspended in 5 ml of methanol, 20 mg of sodium cyanoborohydride and 200 ml of a 10% solution of hydrochloric acid in methanol were added, and the mixture was stirred at room temperature for 30 minutes. The reaction mixture was diluted with a mixed slovent of ethyl acetate/ methyl ethyl ketone, washed with water and an aqueous saturated sodium chloride solution, dried, and concentrated. The residue was put on a Sephadex LH-20 column for chromatography and eluted with methanol. Fractions containing the desired compound were concentrated to dryness to obtain 21 mg of the compound represented by the above formula.

Rf value: 0.29 (Kieselgel 60F₂₅₄ made by Merck Co., developing solvent: acetonitrile:tetrahydrofuran- :toluene:water:acetic acid=4:2:2:0.5:0.1)

FAB-MS(m/z):660(M⁺)

¹H-NMR(300 MHz,DMSO-d₆, δ ppm):11.19(1H,s),9.80 (2H,br),8.86(1H,d,J=9.0 Hz),8.79(1H,d,J=8.7 Hz),7.34(1H, s),7.17(1H,d,J=1.5 Hz),7.04(1H,s),6.97(1H,d,J=1.5 Hz), 6.82(1H,dd,J=1.5,9.0 Hz),6.80(1H,dd,J=8.7,1.5 Hz),5.97 (2H,t,J=5.1 Hz),5.87(1H,br),5.40(1H,t,J=6.0 Hz),5.35(1H, br),5.13(1H,s),4.91 (1H,d,J=3.9 Hz),4.57(2H,d,J=4.2 Hz), 4.20(2H,d,J=4.8 Hz),3.88–4.10(3H,m),3.78(1H,m),3.50 (2H,m)

Example 24

Compound represented by the structural formula

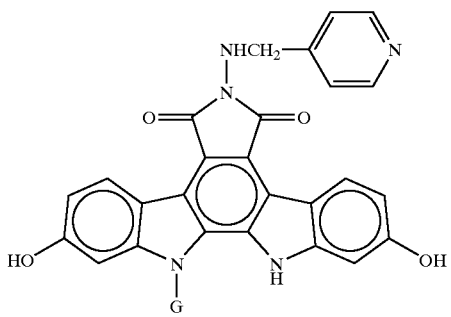

1.0 g of Compound A and 253 mg of 4-pyridinecarbaldehyde were dissolved in 200 ml of methanol, 0.3 ml of acetic acid was added, and the mixture was stirred overnight at 80° C. The deposited crystals were separated by filtration, washed with chloroform, and dissolved in a mixed slovent of methanol/tetrahydrofuran (1:1). 10% palladium-carbon was added, and the mixture was stirred overnight under a hydrogen stream. The mixture was filtered using Celite, and the filtrate was concentrated. The residue was put on a Sephadex LH-20 column for chromatography and eluted with methanol. Fractions containing the desired compound were concentrated to dryness to obtain 730 mg of the compound represented by the above formula.

Rf value: 0.12 (Kieselgel 60F$_{254}$ made by Merck Co., developing solvent: toluene:acetonitrile:tetrahydrofuran:water:acetic acid=2:4:2:0.5:0.1)

FAB-MS(m/z):626(M+H)$^+$ $^1$H-NMR(300 MHz,DMSO-d$_6$, δ ppm):11.18(1H,s),9.80 (2H,br),8.89(1H,d,J=8.3 Hz),8.76(1H,d,J=8.6 Hz),8.49(2H, dd,J=1.8,5.7 Hz),7.55(2H,d,J=6.0 Hz),7.16(1H,d,J=1.5 Hz), 6.97(1H,d,J=2.4 Hz),6.81(2H,dt,J=2.4,8.6 Hz),6.32(1H,t,J= 4.8 Hz),5.96(1H,d,J=9.0 Hz),5.85(1H,br),5.34(1H,br),5.14 (1H,br),4.90(1H,br),4.34(2H,d,J=4.2 Hz),4.00(1H,d,J=11.1 Hz),3.90(2H,br),3.73~3.80(1H,m),3.50(2H,br)

INDUSTRIAL APPLICABILITY

The compounds of the invention have an excellent antitumor effect, and are useful as antitumor agents in the pharmaceutical field.

What is claimed is:

1. A compound represented by the formula:

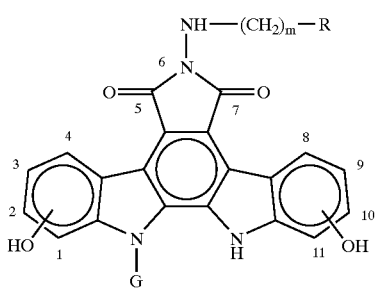

wherein

R represents an unsubstituted pyridyl, unsubstituted furyl or unsubstituted thienyl group, or a pyridyl, furyl or thienyl group each of which has one or more substituents selected from the group consisting of a hydroxyl group, a lower alkoxy group, a hydroxy lower alkyl group and a hydroxy lower alkenyl group except that when the pyridyl, furyl or thienyl group has a lower alkoxy group as a substituent, each of which simultaneously has another substituent selected from the group consisting of a hydroxyl group, a lower alkoxy group, a hydroxy lower alkyl group and a hydroxy lower alkenyl group, m represents an integer of 1 to 3, and G represents a β-D-glucopyranosyl group, and the positions of substitution of the hydroxyl groups on the indolopyrrolocarbazole ring are the 1- and 11-positions, or the 2- and 10-positions, or a pharmaceutically acceptable salt thereof.

2. The compound according to claim 1 represented by the following formula or its pharmaceutically acceptable salt:

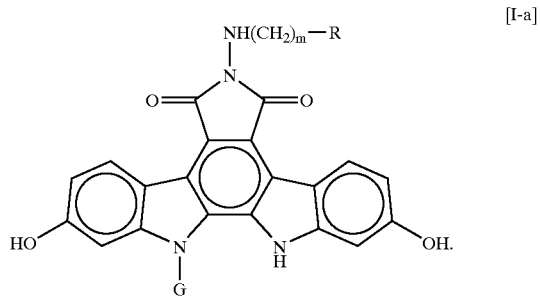

3. The compound according to claim 2 or its pharmaceutically acceptable salt wherein R is a pyridyl group substituted with a hydroxy lower alkyl group.

4. The compound according to claim 3 or its pharmaceutically acceptable salt wherein R is a 6-hydroxymethylpyridin-2-yl group.

5. The compound according to claim 3 or its pharmaceutically acceptable salt wherein R is a 5-hydroxymethylpyridin-4-yl group.

6. The compound according to claim 2 or its pharmaceutically acceptable salt wherein R is a pyridyl group.

7. The compound according to claim 6 or its pharmaceutically acceptable salt wherein R is a pyridin-4-yl group.

8. The compound according to claim 1 represented by the following formula or its pharmaceutically acceptable salt:

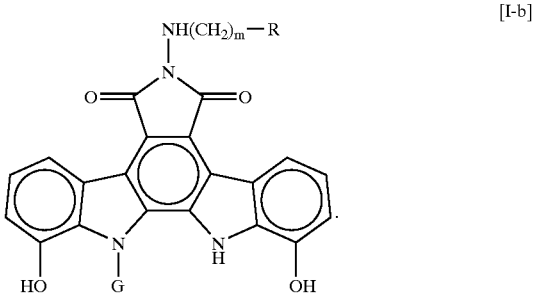

9. A composition comprising a compound or its pharmaceutically acceptable salt according to claim 1, together with an excipient or carrier.

10. A method for treating cancer which comprises administering to a mammal an effective amount of a compound or its pharmaceutically acceptable salt according to claim 1.

11. The method according to claim 10 wherein the mammal is a human.

12. The method according to claim 11 wherein the cancer treated is gastric cancer, colon cancer, lung cancer or breast cancer.

* * * * *